United States Patent [19]
Freedman et al.

[11] Patent Number: 5,766,954
[45] Date of Patent: Jun. 16, 1998

[54] ISOTOPIC COMPOSITION ANALYSER

[75] Inventors: Philip Antony Freedman, Northwich; Timothy Graham Brockwell, Sandbach, both of Great Britain

[73] Assignee: Micromass Limited, Manchester, England

[21] Appl. No.: 635,938

[22] PCT Filed: Sep. 15, 1995

[86] PCT No.: PCT/GB95/02192

§ 371 Date: Apr. 26, 1996

§ 102(e) Date: Apr. 26, 1996

[87] PCT Pub. No.: WO96/08719

PCT Pub. Date: Mar. 21, 1996

[30] Foreign Application Priority Data

Sep. 15, 1994 [GB] United Kingdom ............... 9418638

[51] Int. Cl.[6] .................................................. G01N 33/00
[52] U.S. Cl. .................... 436/144; 436/155; 436/158; 436/159; 436/161; 436/173; 436/181; 436/182
[58] Field of Search .................................. 436/144, 155, 436/158, 159, 161, 173, 181, 182

[56] References Cited

U.S. PATENT DOCUMENTS 4,916,313  4/1990  Hall et al. .......................... 250/282

FOREIGN PATENT DOCUMENTS

| 419167 | 3/1991 | European Pat. Off. |
| 4437120 | 4/1996 | Germany . |
| 9611397 | 4/1996 | WIPO . |

OTHER PUBLICATIONS

J. Bigeleisen et al. *Anal. Chem. 1952*, 24, 1356–1357.
C. Genty et al. *Anal. Chem. 1970*, 42, 7–11.
W.M. Thunston *Rev. Sci. Instrum. 1970*, 41, 963–966.
A. Runge *Chem. Abstr. 198, 93*, 36301h.
W.W. Wong et al. *Anal. Chem. 1984*, 56, 1852–1858.
P. Harting *Chem. Abstr. 1989*, 111, 157102t.
A. Schimmelmann et al. *Anal. Chem. 1993*, 65, 789–792.
M. Gehve et al. *Anal. Chem. 1996* 68, 4414–4417.
Zeitchrift Fur Analytische Chemie, "Einstufige Umargeitung organischer Verbindungen in Wasserstoff zur massenspektrometrischen Isotopenanalyse", W. Rolle and H. Hubner, vol. 232 (1967) pp. 328–331, and translation.
Analytical Chemistry, "Chemistry of Hydrogen Gas Preparation by Pyrolysis for the Measurement of Isotope Ratios in Hydrocarbons", Zvi Sofer, vol. 58 (1986), pp. 2029–2032.

*Primary Examiner*—Arlen Soderquist
*Attorney, Agent, or Firm*—Alix, Yale & Ristas, LLP

[57] ABSTRACT

A continuous flow method of determining the quantitative isotopic composition of hydrogen comprised in a compound is disclosed, together with apparatus for carrying out the method. The method involves introducing the sample to be analysed into a flow of carrier gas which does not contain hydrogen, the carrier gas then being arranged to flow through a heated catalytic reactor which contain a chromium-based catalyst. The sample is pyrolysed in the catalytic reactor so as to form molecular hydrogen which is then analysed mass-spectrometrically. Preferably a gas chromatograph is disposed before the catalytic reactor so that one or more components or a mixture may be separately analysed.

20 Claims, 2 Drawing Sheets

ISOTOPIC COMPOSITION ANALYSER

This is a National Stage Application of PCT application No. PCT/GB95/02192 filed Sep. 15, 1995.

BACKGROUND OF THE INVENTION

1. Field of the Invention

This invention relates to a method of determining the quantitative isotopic composition of hydrogen comprised in a compound, and to apparatus for carrying out the method.

2. Description of the Prior Art

The isotopic analysis of the hydrogen contained in an organic compound is a matter of wide interest in fields varying from petrochemicals to space science. However, present methods of determining the isotopic composition of hydrogen are laborious, time-consuming and suffer from many problems such as isotopic fractionation, memory effects and the fact that many materials are permeable to hydrogen gas. Typically, the time taken for a single isotopic analysis is of the order of tens of minutes, and after one analysis has been performed, a longer period of time elapses before it is possible to perform another analysis. Further, present methods do not allow separate isotopic analysis of the hydrogen contained in several compounds in a mixture of compounds.

One method commonly used to isotopically analyse the hydrogen contained in an organic sample involves the combustion of the organic matter to carbon dioxide and water. The water is cryogenically separated from the $CO_2$ and passed over hot uranium or zinc shavings in order to reduce it to hydrogen gas, which is then mass-spectrometrically analyzed to give the isotopic composition. This procedure is slow, and is liable to the problem of isotope fractionation, so that an accurate isotopic analysis is not obtained.

A solution to these problems was suggested by Zvi Sofer (Anal. Chem. Volume 58, 1986, pp 2029–2032 "Chemistry of Hydrogen Gas Preparation by Pyrolysis for the Measurement of Isotope Ratios in Hydrocarbons".) This method involves the direct pyrolysis of the hydrocarbon to hydrogen gas at elevated temperatures, (>900° C.). The gas formed by pyrolysis is then isotopically analyzed using a mass spectrometer. The result is corrected by a factor that takes into account the isotope fractionation effect. This factor is calculated from the rate constants of the reactions taking place, and is only accurate if there are no other elements present apart from carbon and hydrogen, so that this method is only suitable for hydrocarbons of the type $C_xH_y$, and must take place inside a sealed system, which adds to its complexity.

Harting (Isotopenpraxis, 1989 vol 25 (8) pp 347–348) teaches another batch process for the conversion of hydrocarbons to hydrogen. The analyte is pyrolyzed at a temperature of 1000°–1300° K. in an evacuated quartz furnace packed with a Chromium catalyst for between 5 and 30 minutes. The hydrogen so produced may then be manually transferred into the inlet system of a mass spectrometer using a Toepler pump. Complete transfer of the sample is necessary to avoid errors due to fractionation so that the process is very time-consuming. Harting's experiments suggest that the catalytic reaction produces substantially complete conversion in 5 minutes at 1300° K. and that no significant errors are introduced by diffusion of the hydrogen through the walls of the quartz furnace.

A much faster general method for the isotopic analysers analysis of organic compounds is taught in EP 0419167. A sample comprising a mixture of analytes is injected into a flow of an inert carrier gas (e.g. helium) substantially at atmospheric pressure and the resulting flow passed through a gas-chromatographic column in order to separate the analytes. The effluent from the column is passed, again at atmospheric pressure, through a catalytic conversion furnace, typically comprising a Pt/Rh catalyst maintained at 1200° C., so that hydrocarbon analytes are converted to carbon monoxide, molecular hydrogen and molecular nitrogen. These gases, and the inert carrier gas are then introduced into the source of an isotopic-ratio mass spectrometer via a pressure-reduction stage. It has been found, however, that this method is of limited accuracy for hydrogen isotopic ratio determination because the Pt/Rh catalyst absorbs hydrogen, leading to large fractionation errors.

Unfortunately, the prior "static" vacuum methods of hydrogen conversion for isotopic-ratio determination, e.g. Sofer and Harting, do not help in the discovery of a better catalyst for a continuous-flow method of analysis because the conditions under which they are used are very different. In a continuous-flow method the requirement for fast complete conversion is much more onerous than in the static methods because of the shorter residence time. Further, it is probable that adsorption of the inert gas on the catalyst surface in the continuous-flow method will reduce the active surface area of the catalyst and slow down the conversion process. In addition, the reduction reaction typically will involve a volume increase as, for example, in the reaction quoted by Harting:

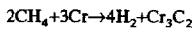

$$2CH_4 + 3Cr \rightarrow 4H_2 + Cr_3C_2$$

Consequently, increasing the inert-gas pressure will, according to Le Chatelier's principle, shift the equilibrium state of the reaction away from complete conversion. One may therefore conclude that as Harting still found it necessary to allow five minutes for the conversion under static high vacuum conditions, it would be unlikely that the catalysts he suggests would be suitable for a continuous-flow conversion system operating at high pressure with a large excess of inert gas.

SUMMARY OF THE INVENTION

The present invention addresses the problems of the prior art methods.

Thus, in one aspect the invention provides a continuous flow method of determining the isotopic composition of hydrogen in a sample, said method comprising the sequential operation of the following steps:

i) causing a carrier gas which does not comprise hydrogen to flow at atmospheric pressure or above through a heated catalytic reactor comprising a catalyst;

ii) introducing said sample into said flow of carrier gas before it enters said catalytic reactor so that said sample is pyrolyzed in said reactor, and any hydrogen present in said sample is converted to molecular hydrogen;

iii) conveying at least some of the gases emerging from said catalytic reactor into a mass spectrometer; and iv) determining the isotopic composition of the said molecular hydrogen by mass spectrometric measurements, wherein the catalyst contained in the said catalytic reactor comprises chromium maintained at a temperature of between 850° and 1000° C.

The method of the invention provides a continuous-flow method of determining the isotopic ratio of hydrogen contained in a sample. It further allows the accurate measuring of hydrogen isotopes, avoiding isotope, fractionation and memory effects. Furthermore, the present invention provides an improved method for measuring hydrogen isotope ratios which is fast and does not involve the time-consuming manual recirculation of the sample. The invention moreover allows the measuring of hydrogen isotope ratios in various successive samples, including hydrocarbons, organic compounds and water, accurately and at speed.

The catalyst may comprise a mixture of two or more of chromium metal, a chromium compound and a chromium alloy. It is preferred that the catalyst itself is substantially completely of chromium metal, a chromium compound or a chromium alloy, or a mixture thereof. The chromium-based component may also be present as a mixture with other conventional materials.

The catalyst may be in one of many forms. Thus, it is preferred that the catalyst comprises a powder or granules of chromium metal, a chromium compound (e.g. chromium oxide, $Cr_2O_3$), or a chromium alloy, or a mixture containing one or more of such components; such powders or granules are commercially available.

Further, the catalyst in the catalyst reactor may be in the form of a zeolite (or a similar structure), the chromium-containing substance being incorporated within it. The catalyst may also be in the form of a mesh, wire or any other suitable form; Nichrome wire is particularly preferred.

The catalytic reactor is heated to and maintained at a temperature between 850°–1000° C., and most preferably at approximately 950° C.

The method of the invention may be used for the determination of the hydrogen isotope ratio of a. hydrocarbon or a more complex organic compound. In particular also, the invention provides a convenient and accurate method for the determination of the isotopic composition of hydrogen in water.

A preferred method according to the invention comprises the additional step of passing the carrier gas carrying said sample through a chromatographic column prior to its admission to the catalytic reactor. In this way individual constituents comprised in a sample which is a mixture may be temporally separated by the column and enter the catalytic reactor sequentially allowing their hydrogen isotopic compositions to be determined separately. Use of a chromatographic column is also preferred even if the sample is a pure compound because it extends the time during which the sample enters the furnace, resulting in more time in which the mass spectrometric analyses may be carried out. The chromatographic column and conditions are selected to provide good resolution of the constituents of a mixture whose isotopic compositions are to be determined. In addition the invention allows the measuring of isotope ratios of the hydrogen comprised in at least some of the components of a mixture without the need to prepare samples of the pure components.

The chromatographic system employed preferably incorporates facilities for allowing only selected constituents to enter the catalytic reactor. This is especially useful when it is necessary to determine the isotopic composition of only a few constituents of a complex mixture.

Preferably, a system similar to that disclosed in EP-A-306332 or U.S. Pat.No. 4916313 may be employed. This system provides a chromatographic arrangement which maintains a constant flow of carrier gas into the mass spectrometer under all circumstances. It further provides a method of introducing one or more reference gases into the mass spectrometer at times when no component of interest is eluting from the column, thereby increasing the accuracy of the isotope ratio measurements.

Viewed from another aspect the invention provides apparatus for the continuous flow determination of the isotopic composition of hydrogen comprised in a sample, said apparatus comprising:

i) a catalytic reactor comprising a catalyst and arranged for the pyrolysis of samples introduced therein;

ii) means for maintaining said catalyst at a temperature between 850° C. and 1000° C.;

iii) means for introducing a said sample into a flow of carrier gas which does not contain hydrogen;

iv) first conduit means for conveying said carrier gas from said means for introducing said sample to said catalytic reactor at atmospheric pressure or above, whereby said sample is pyrolyzed in such a way that any hydrogen in it is converted to molecular hydrogen;

v) a mass spectrometer for determining the isotopic composition of hydrogen in the form of molecular hydrogen;

vi) second conduit means for conveying effluent from said catalytic reactor to said mass spectrometer; wherein said catalyst comprises chromium.

In a preferred embodiment, the apparatus according to the invention further comprises a gas-chromatographic column disposed between the means for introducing the sample and the catalytic reactor, whereby the isotopic composition of at least some of the constituents of a mixture may be determined.

The catalytic reactor may conveniently comprise a quartz capillary tube approximately 0.5 mm internal diameter and 0.5 m long, partially packed with commercially available chromium powder. This is heated to a temperature in the range 850°–1000° C. by means of an electrically heated furnace surrounding the capillary tube. A reactor of this type is described in EP-A-306332 and U.S. Pat.No. 4916313.

BRIEF DESCRIPTION OF THE DRAWING

Preferred embodiments of the invention will now be described in greater detail by way of example only and with reference to the accompanying drawings in which.

DESCRIPTION OF THE DISCLOSED EMBODIMENT

Figure 1:
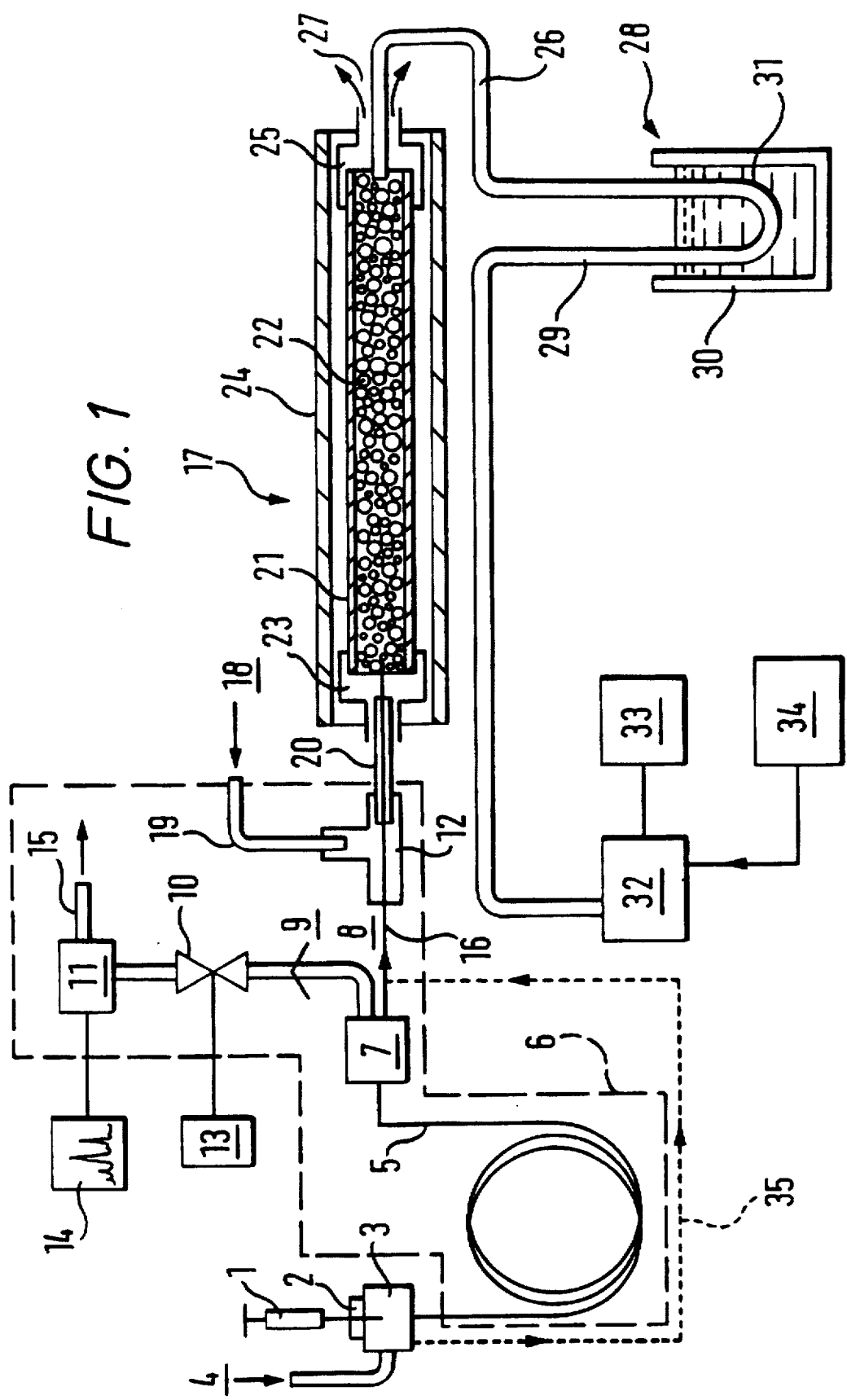
FIG. 1 is a schematic diagram of a preferred embodiment of the apparatus of the invention.

Referring to FIG. 1, a solution of a sample to be analysed is contained in a syringe 1. To start an analysis, the solution in syringe 1 is injected through septum 2 into an injector 3 where it mixes with a carrier gas 4 and is carried onto a gas chromatographic column 5. Column 5 is preferably a capillary column disposed inside a conventional gas chromatographic oven schematically shown at 6. Injector 3 is preferably also heated, either by the column oven 6 or a separate oven (not shown).

Column 5 terminates inside the oven in an effluent splitter 7 which, together with valve 10 provides means for admitting into the mass spectrometer gas which has passed through the column 5. Splitter 7.divides the flow between two routes 8 and 9. The flow along route 9 passes through valve 10 to a suitable chromatographic detector 11, typically a flame ionization detector. The flow along route 8 passes through a make-up tee 12, described in detail below, to a sample conversion means 17.

Splitter 7, valve 10, detector 11 and make-up tee 12 are all installed inside oven 6 so that they are maintained at the column operating temperature. Valve 10 is operated by a pneumatic actuator 13 located outside oven 6, and detector 11 is connected to a chromatograph data acquisition system.

After passing through detector 11, effluent flowing along route 9 passes through vent 15 to discharge at atmospheric pressure. When valve 10 is open, substantially all the column effluent will follow this route because the impedance it presents is very much less than the impedance presented by route 8 and the conversion means 17. Thus, by closing valve 10, column effluent is forced to flow through capillary 16 which is typically made of the same type of tubing as column 5 (e.g. 0.20 mm bore quartz capillary tube). Capillary 16 extends right through make-up tee 12 and into the sample conversion means 17, and a second flow of carrier gas 18 is introduced into tee 12 through pipe 19. An outlet pipe 20 is fitted to the third port of the tee.

Capillary 16 extends inside tube 20 so that the carrier gas entering through pipe 19 flows in the annular space between the exterior of capillary 16 and the inside wall of tube 20. This arrangement ensures turbulent mixing of the gases as they enter the sample conversion means 17.

Pipe 20 and capillary 16 are heated between oven 6 and the conversion means 17 by means of a heating oven (not shown) which maintains their temperature at least as high as the column temperature, thereby preventing condensation of the sample.

Sample conversion means 17 comprises a quartz tube 21 which is partially packed with a catalyst 22. Pipe 20 is connected to tube 21 by means of a reducing coupling 23, through which capillary 16 extends into catalyst 22, which is capable of converting the hydrogen present in the sample into molecular hydrogen.

Preferably, catalyst 22 comprises commercially available chromium granules of 0.3–0.4 mm diameter. Alternatively, catalyst 22 may comprise chromium oxide powder or granules, or another chromium-containing compound or mixture. The catalyst may alternatively be in the form of a zeolite (or a similar structure), the chromium-containing substance being incorporated within it. The catalyst may also be in the form of a mesh, wire or any other suitable form—Nichrome wire being an example.

Tube 21 is heated by an electrically heated furnace 24 which surrounds tube 21. Effluent from the tube 21, which now comprises molecular hydrogen mixed with the carrier gas (typically helium), passes through a reducing coupling 25 into pipe 26. An open split 27 is conveniently provided by ensuring that the inside diameter of coupling 25 is greater than the outside diameter of pipe 26, as shown. A small portion of the flow of hydrogen and carrier gas leaves tube 21 in pipe 26 and enters a coiled tube 29 in trapping means 28, which is adapted to remove unwanted components from the gas flow. Trapping means 28 comprises the coiled tube 29 immersed in liquid nitrogen 31 contained in an insulated vessel 30.

The outlet of trapping means 28 is taken to one inlet of a conventional multi-collector isotope-ratio mass spectrometer 32, which has two inlet ports and a computerized data acquisition system 33. The other inlet of mass spectrometer 32 is connected to a reference gas introducing means 34, for introducing into the mass spectrometer a calibration sample of a reference gas of accurately known isotopic composition. A suitable construction for reference gas introducing means 34 is shown in EP-A-306332 and U.S.Pat. No. 916313.

If it is desired to perform the isotopic analysis of the hydrogen contained in water samples, injector 3 may be connected directly to capillary 16 by connecting tube 35 (shown as a dotted line in FIG. 1.), so that the water samples do not pass through the Gas Chromatographic segment of the apparatus.

A preferred method of operating the apparatus is as follows:

First, the interface system and a chromatographic column which will separate the components to be analyzed are conditioned in the normal way until a steady and small background signal is observed on the mass spectrometer. The sample is injected from syringe 1 on to the column 5 with valve 10 open so that column effluent is routed through the detector 11 and subsequently vented. Meanwhile, one or more calibration samples may be admitted into the mass spectrometer. The isotopic composition of these is measured in a conventional way.

Once the solvent and any unwanted components prior to the peak to be analyzed have eluted from column 5, valve 10 is closed to allow substantially all of the peak to pass into the conversion means 17 where it is converted into hydrogen gas suitable for admission into the mass spectrometer. Selective trapping means 28 removes unwanted material from the effluent of the conversion means, which is then admitted into the spectrometer. The isotopic ratio of the hydrogen contained in the sample under investigation is then determined by integrating with respect to time the outputs of the mass spectrometer. This should be carried out over the entire chromatographic peak to ensure that fractionation effects during the chromatograph separation or conversion do not adversely affect the measurement.

As soon as substantially all of the converted sample has been analyzed, valve 10 is opened and more calibration samples are admitted. The isotopic composition of the sample is determined using the results of the calibration sample in a conventional way.

If the sample in syringe 1 is a mixture, other components eluting from the column may be analyzed during a single run, interspersing calibration samples between the peaks whenever possible. If the time between two peaks is too short to allow a calibration sample to be inserted, these peaks may be analyzed consecutively using calibration samples analyzed on either side of the pair.

It will be appreciated that the whole apparatus is preferably automated and under the control of the computerized data acquisition system 33, which is also programmed to carry out the integration as discussed above. The acquisition system 33 may also conveniently be programmed to control valve 10 and reference gas introducing means 34, and also an automatic injector if available, to admit the sample to be analyzed and calibration samples according to the invention making due allowance for the time delays introduced by the column 5 and the conversion means 17, which are determined by previous experiments. Automation of the remainder of the system is conventional and need not be described in detail.

EXAMPLE

In order to compare results obtained using the method and apparatus according to the invention, five hydrocarbon samples (decane, undecane, dodecane, hexadecane and eicosane) were isotopically analysed by a conventional analytical method and by the method of the invention. The conventional method involved combustion of each of the samples in sealed tubes in the presence of copper oxide (CuO). The continuous flow method of analysis described in EP 0419167, using a uranium catalyst in the furnace, was used to reduce the water so produced and to determine the isotopic composition of the hydrocarbons. For the method according to the invention a mixture of the hydrocarbons was prepared and 29 samples were analysed using a gas chromatograph to separate the individual constituents as previously described. Table 1 is a comparison of the delta values δD (‰) values obtained by both methods.

TABLE 1

| Method | δ D (%) | | | | |
|---|---|---|---|---|---|
| | Decane | Undecane | Dodecane | Hexadecane | Eicosane |
| Conventional | −93.7 | −221.1 | −120.5 | −105.5 | −58.5 |
| Invention | −99.6 | −227.8 | −134.6 | −124.0 | −56.1 |
| Std. Deviation | 4.7 | 5.2 | 10.0 | 8.5 | 7.4 |

Figure 2:
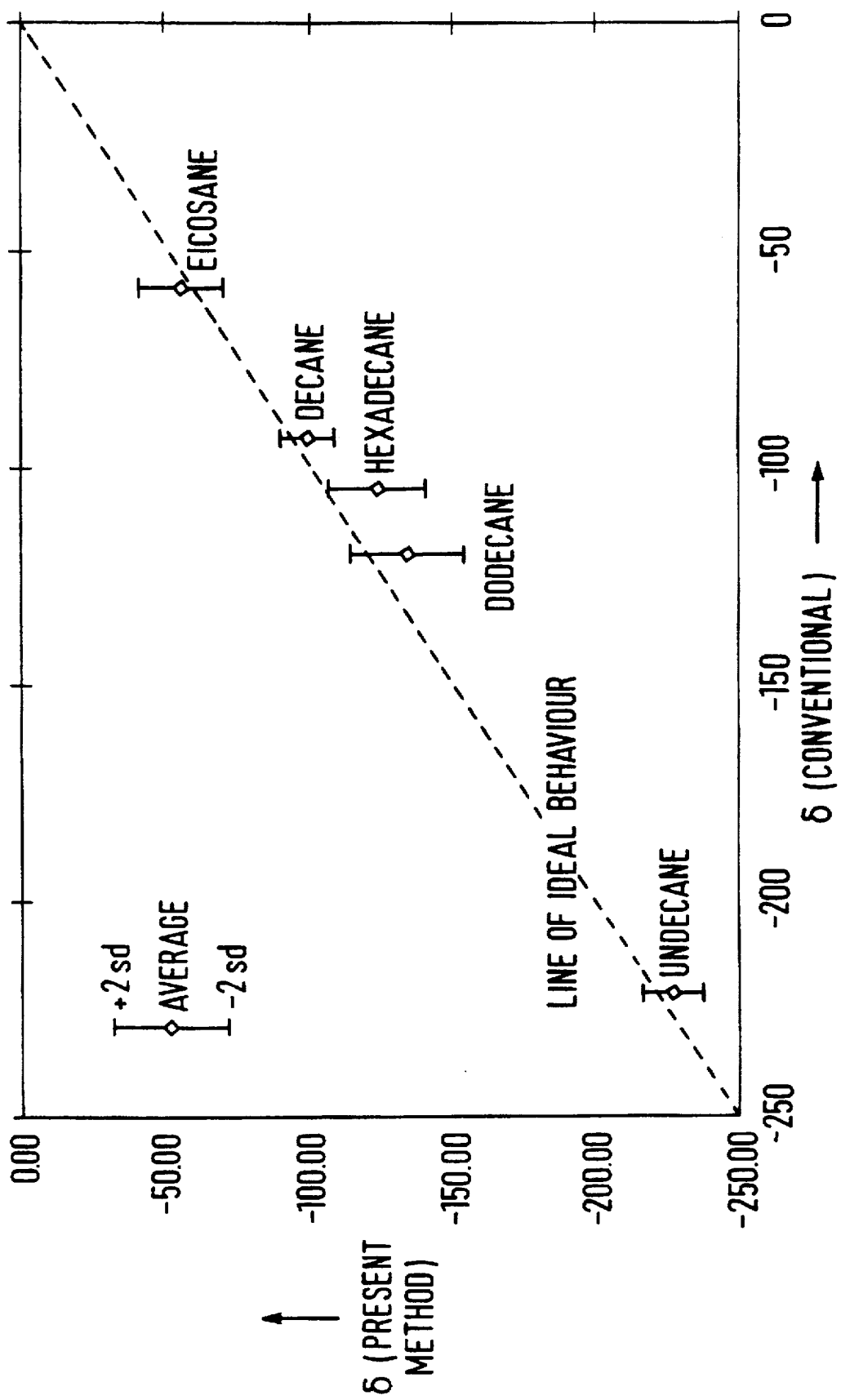
FIG. 2 is a graphical comparison of the results obtained for the analysis of certain hydrocarbons using a conventional method and the method of the invention.

FIG. 2 shows the data of Table 1 in a graphical format, in which the error bars represent the standard deviations and the dotted line represents exact agreement between the two methods. It is clear that the method of the invention produces good agreement with the results obtained by the conventional method, and as explained, is very much faster and more convenient than the prior methods.

We claim:

1. A continuous-flow method of determining the isotopic composition of hydrogen in a sample, said method comprising the sequential performance of the following steps:

i) causing a carrier gas which does not contain hydrogen to flow at a pressure at least as great as atmospheric pressure through a heated catalytic reactor comprising a catalyst;

ii) introducing a sample into said flow of carrier gas before it enters said catalytic reactor so that said sample is subsequently pyrolyzed in said reactor, pyrolyzation causing any hydrogen present in said sample to be converted to molecular hydrogen;

iii) conveying at least some of the gases emerging from said catalytic reactor into a mass spectrometer; and iv) determining the isotopic composition of said molecular hydrogen by mass spectrometric measurements;

wherein said catalyst is a material comprising chromium maintained at a temperature between 850° C. and 1000° C.

2. A method as claimed in claim 1 comprising the additional step of passing the carrier gas carrying said sample through a chromatographic column prior to its admission to said catalytic reactor, whereby individual constituents comprised in a said sample may be temporally separated by said chromatographic column to allow their hydrogen isotopic compositions to be separately determined.

3. A method as claimed in claim 1 wherein said catalyst is a material selected from the group consisting of:

i) metallic chromium;

ii) a chromium containing alloy; and iii) a chromium containing compound.

4. A method as claimed in claim 1 wherein said catalyst comprises a mixture of at least two materials selected from the group consisting of:

i) metallic chromium;

ii) a chromium containing alloy; and iii) a chromium containing compound.

5. A method as claimed in claim 1 wherein said catalyst is in powdered or granular form.

6. A method as claimed in claim 5 wherein said catalyst comprises chromium oxide ($Cr_2O_3$).

7. A method as claimed in claim 1 wherein said catalyst is in a mesh or wire form.

8. A method as claimed in claim 7 wherein said catalyst comprises Nichrome wire.

9. A method as claimed in claim 1 wherein said catalyst is maintained at a temperature of approximately 950° C.

10. Apparatus for the continuous flow determination of the isotopic composition of hydrogen comprised in a sample, said apparatus comprising:

i) catalytic reactor means for the pyrolysis of samples introduced therein, said reactor including a catalyst which comprises chromium;

ii) means for maintaining said catalyst at a temperature between 850° C. and 1000° C.;

iii) means for introducing a sample into a flow of carrier gas which does not contain hydrogen;

iv) first conduit means for conveying said carrier gas from said means for introducing said sample to said catalytic reactor at a pressure which is at least as high as atmospheric pressure whereby said sample is pyrolyzed to convert any hydrogen in said sample to molecular hydrogen;

v) a mass spectrometer for determining the isotopic composition of hydrogen in the form of molecular hydrogen;

vi) second conduit means for conveying effluent from said catalytic reactor to said mass spectrometer.

11. Apparatus as claimed in claim 10 comprising a gas-chromatographic column disposed between said means for introducing a sample and said catalytic reactor, whereby the isotopic composition of individual constituents comprised in a said sample may be temporally separated to allow the hydrogen isotopic compositions to be separately determined.

12. Apparatus as claimed in claim 11 wherein said catalyst is a material selected from the group consisting of:

i) metallic chromium;

ii) a chromium containing alloy; and iii) a chromium containing compound.

13. Apparatus as claimed in claim 11 wherein said catalyst comprises a mixture of at least two materials selected from the group consisting of:

i) metallic chromium;

ii) a chromium containing alloy; and iii) a chromium containing compound.

14. Apparatus as claimed in claim 10 wherein said catalyst is a material selected from the group consisting of:

i) metallic chromium;

ii) a chromium containing alloy; and iii) a chromium containing compound.

15. Apparatus as claimed in claim 10 wherein said catalyst comprises a mixture of at least two materials selected from the group consisting of:

i) metallic chromium;

ii) a chromium containing alloy; and iii) a chromium containing compound.

16. Apparatus as claimed in claim 10 wherein said catalyst is in powdered or granular form.

17. Apparatus as claimed in claim 16 wherein said catalyst comprises Chromium oxide ($Cr_2O_3$).

18. Apparatus as claimed in claim 10 wherein said catalyst is in a mesh or wire form.

19. Apparatus as claimed in claim 18 wherein said catalyst comprises Nichrome wire.

20. Apparatus as claimed in claim 10 wherein said means for maintaining said catalyst at a temperature between 850° C. and 1000° C. maintains said catalyst at a temperature of approximately 950° C.

* * * * *